US008585625B2

(12) United States Patent
Hegland

(10) Patent No.: US 8,585,625 B2
(45) Date of Patent: Nov. 19, 2013

(54) BOUTONNIERE DEFORMITY RING SPLINT

(76) Inventor: June M. Hegland, St. Louis Park, MN (US)

(*) Notice: Subject to any disclaimer, the term of this patent is extended or adjusted under 35 U.S.C. 154(b) by 273 days.

(21) Appl. No.: 13/107,453

(22) Filed: May 13, 2011

(65) Prior Publication Data
US 2012/0289876 A1 Nov. 15, 2012

(51) Int. Cl.
A61F 5/00 (2006.01)

(52) U.S. Cl.
USPC .......................................................... 602/22

(58) Field of Classification Search
USPC .......... 602/5, 12, 22, 30; 128/878–880; 5/623
See application file for complete search history.

(56) References Cited

U.S. PATENT DOCUMENTS

| 440,434 | A | * | 11/1890 | Mocarty | 602/30 |
| 1,561,631 | A | * | 11/1925 | Winter | 128/880 |
| 1,733,933 | A | * | 10/1929 | Beltz | 128/880 |
| 3,170,460 | A | * | 2/1965 | Stilson | 602/22 |
| 4,243,026 | A | * | 1/1981 | Barber | 602/22 |
| 4,270,528 | A | * | 6/1981 | Hanson | 602/22 |
| 4,441,489 | A | * | 4/1984 | Evans et al. | 602/22 |
| 4,932,396 | A | * | 6/1990 | Garris | 602/22 |
| 5,012,799 | A | * | 5/1991 | Remmen | 602/30 |
| 5,020,524 | A | * | 6/1991 | Donohue | 602/22 |
| 5,376,091 | A | * | 12/1994 | Hotchkiss et al. | 606/55 |
| 5,681,269 | A | * | 10/1997 | Basaj et al. | 602/22 |
| 5,848,983 | A | * | 12/1998 | Basaj et al. | 602/22 |
| 6,110,136 | A | * | 8/2000 | Belkin | 602/22 |
| 8,235,928 | B2 | * | 8/2012 | Padova | 602/22 |
| 8,262,599 | B2 | * | 9/2012 | Chandrasekar et al. | 602/20 |
| 2002/0129619 | A1 | | 9/2002 | Wolff | |
| 2006/0094989 | A1 | * | 5/2006 | Scott et al. | 601/5 |
| 2007/0017252 | A1 | | 1/2007 | Yoshida et al. | |
| 2009/0099493 | A1 | | 4/2009 | Barnes | |
| 2009/0326428 | A1 | | 12/2009 | Farrell et al. | |

OTHER PUBLICATIONS

Jessica, Ring O Blog, "Sterling Silver Filigree Armor Ring," http://ringoblog.com/ring-by-type/sterling-silver-rings/sterling-silver-filigree-ring/, Sep. 10, 2010 (1 page).

* cited by examiner

Primary Examiner — Patricia Bianco
Assistant Examiner — Raymond E Harris
(74) Attorney, Agent, or Firm — Allison Johnson; Allison Johnson, P.A.

(57) ABSTRACT

A ring splint that includes a first loop, a second loop, a third at least partial loop, and an elongated support, the first loop and the second loop being attached to the support, the elongated support exhibiting a rigid property and a flexible property such that the elongated support maintains a finger in at least partial extension when the ring is on a finger and the elongated support is in contact with the palmar surface of the finger and flexes when the user bends the finger.

20 Claims, 4 Drawing Sheets

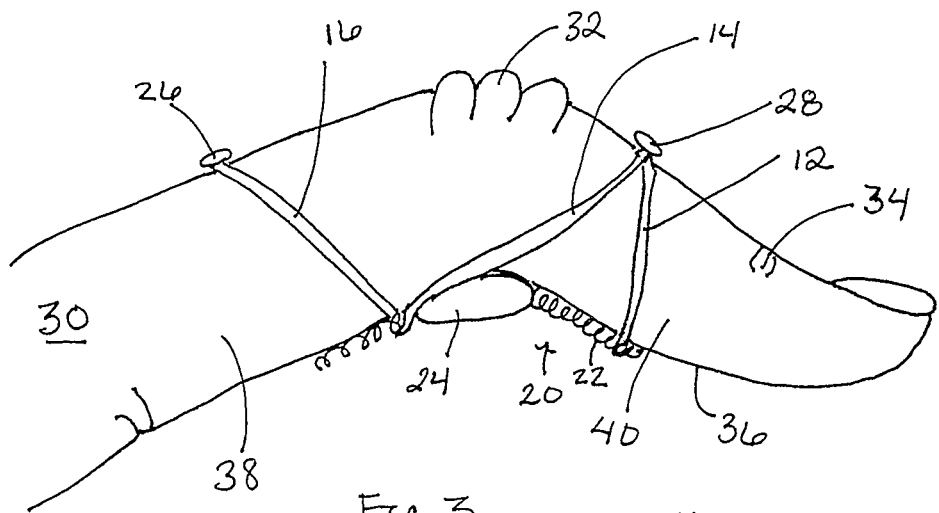
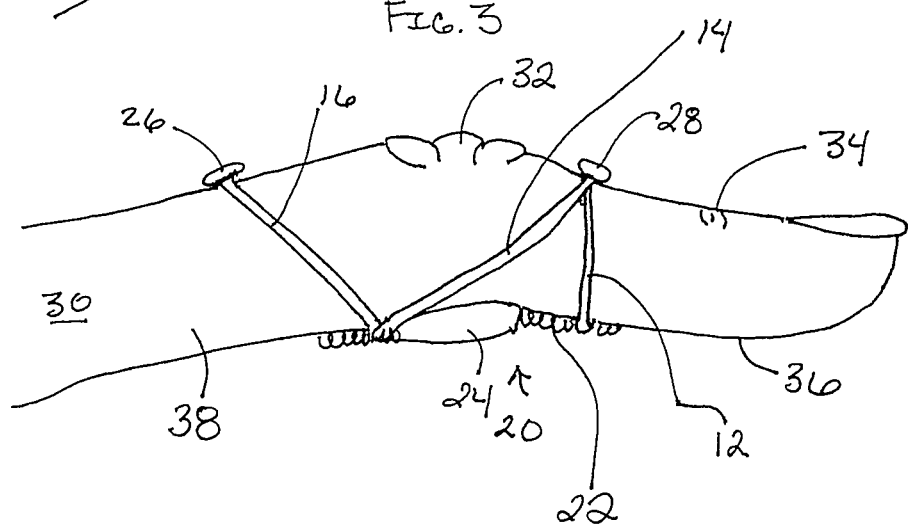
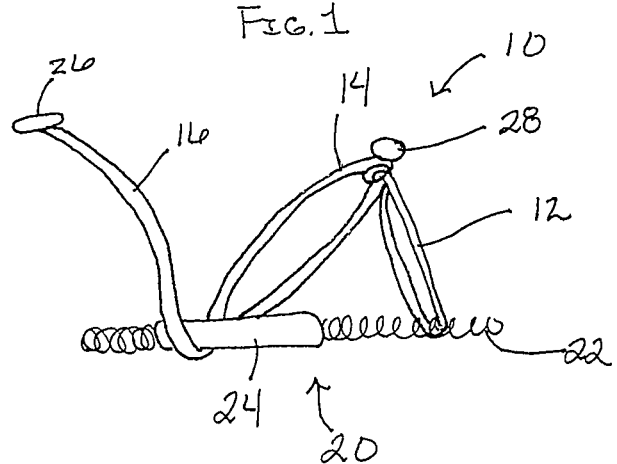

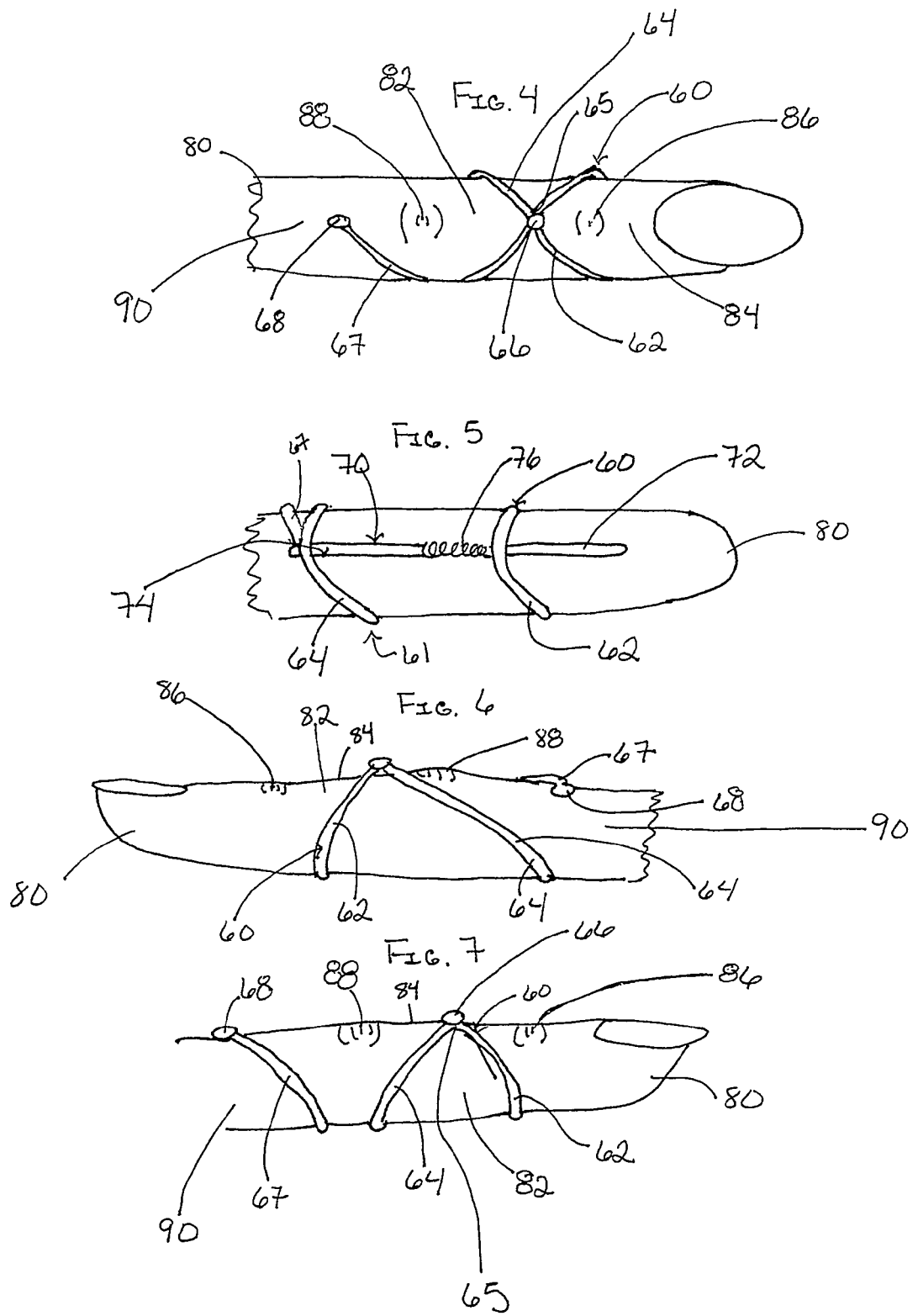

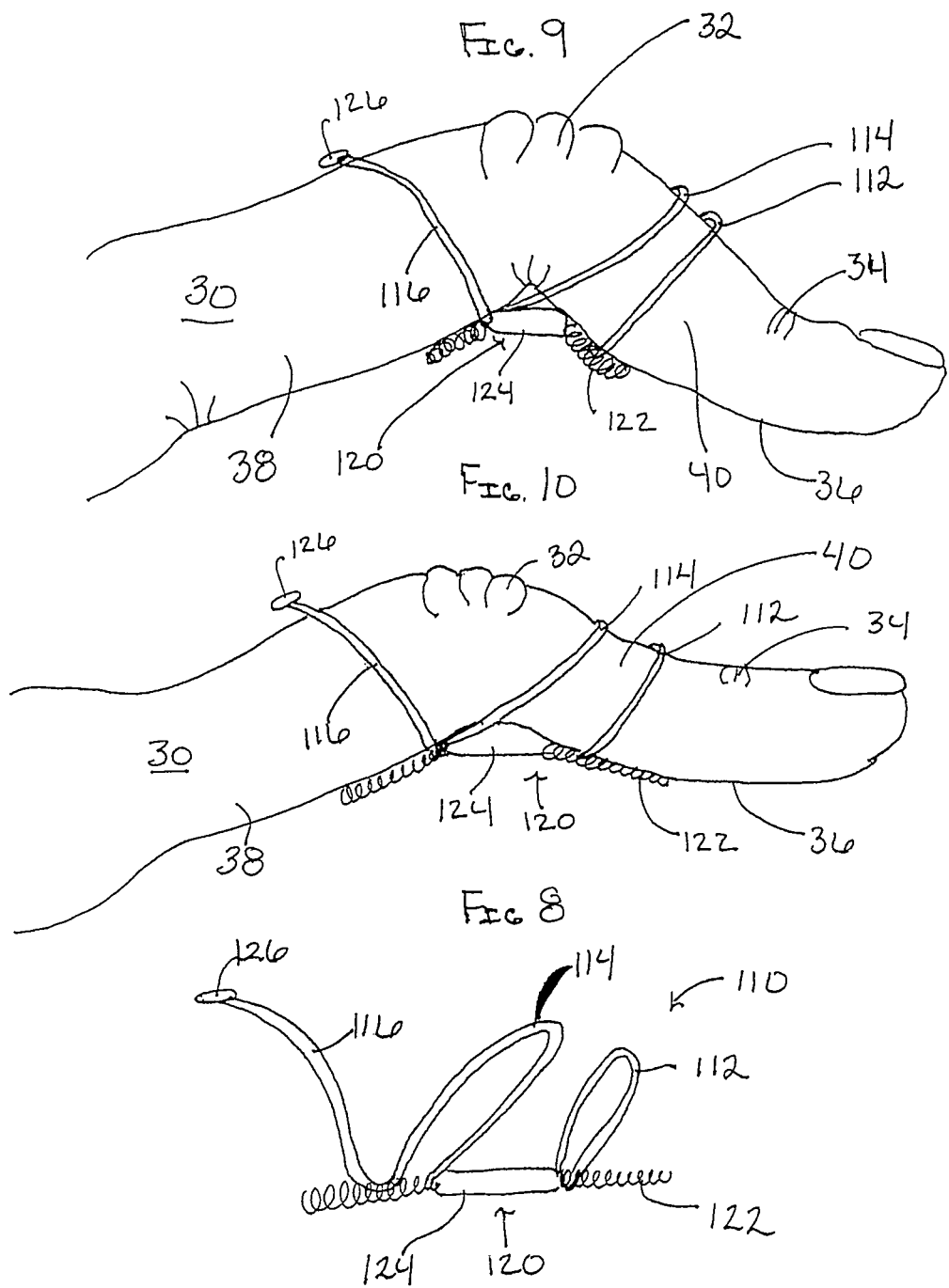

BOUTONNIERE DEFORMITY RING SPLINT

BACKGROUND

The invention relates to applying an extension force to a boutonniere deformity.

Boutonniere deformities occur in fingers and consist of a proximal interphalangeal joint that is flexed and a distal interphalangeal joint that is hyperextended. This deformity makes it difficult or impossible to extend the proximal interphalangeal joint. It is commonly caused by injury or by an inflammatory condition like rheumatoid arthritis.

A pseudoboutonniere deformity is a condition marked by proximal interphalangeal joint flexion contracture and restricted flexion of the distal interphalangeal joint. The characteristic hyperextension of the distal interphalangeal in boutonniere deformities is not present in pseudoboutonniere deformities.

Ring splints have been developed to straighten or realign interphalangeal joints of fingers and thumbs. One such ring splint includes two elliptical rings joined by an elliptical spacer as described in U.S. Pat. No. 4,932,396. The ring splint disclosed in U.S. Pat. No. 4,932,396 is described as being worn with the spacer over the joint on a boutonniere finger or mallet finger. In such a position, the ring splint is described as being capable of holding the finger in extension.

SUMMARY

In one aspect, the invention features a ring splint that includes a first loop, a second loop, a third at least partial loop, and an elongated support, the first loop and the second loop being attached to the support, the elongated support exhibiting a rigid property and a flexible property such that the elongated support maintains a finger in at least partial extension when the ring is on a finger and the elongated support is in contact with the palmar surface of the finger, and flexes when the user bends the finger. In one embodiment, the second loop terminates in the third at least partial loop. In another embodiment, the first loop is attached to the second loop.

In some embodiments, the support includes a hinge. In one embodiment, the support includes at least one of a living hinge and a spring hinge.

In other embodiments, the support includes a spring. In one embodiment, the support includes a spring that includes a first end, a first elongate section attached to the first end of the spring, and a second elongate section attached to the second end of the spring.

In another embodiment, the support includes a longitudinal extent and a cushion enveloping at least a portion of the longitudinal extent.

In some embodiments, the support is removably attached to the first and second loops. In other embodiments, the support is repeatedly repositionable within the first and second loops.

In another embodiment, the ring is in position on the finger the support is positioned between the palmar surface of the finger and the first and second loops.

In other embodiments, the ring splint further includes an ornamental component. In another embodiment, the ring splint further includes an ornamental component on at least one of the second loop and the third at least partial loop.

In another embodiment, the ring splint includes a first loop, a second loop, the first loop being attached to the second loop, a third at least partial loop, and an elongated support attached to the first and second loops and exhibiting rigid properties and flexible properties such that the elongated support maintains a finger in at least partial extension when the splint is in position on a finger and flexes when the user bends the finger.

In other aspects, the invention features method of using the ring splint of claim 1, the method including positioning the third at least partial loop around a portion of the proximal phalanx of a finger, positioning the second loop around the intermediate phalanx, positioning the first loop around the intermediate phalanx, and positioning the elongated support against at least a portion of the palmar surface of the finger.

In another aspect, the invention features a finger ring that includes a first loop, a second loop, and a third at least partial loop, the first loop and the second loop being attached to one another at a first location, the third loop extending from the second loop, such that when the ring is positioned on a finger, the first loop loops around the intermediate phalanx of the finger, the second loop loops around the intermediate phalanx of the finger, the third at least partial loop loops around a portion of the proximal phalanx of the finger and the first location is positioned on the dorsal surface of the intermediate phalanx of the finger. In one embodiment, the third at least partial loop forms a spiral with the second loop. In other embodiments, the third at least partial loop is attached to the second loop.

When worn on a finger, the ring exerts a force against the finger that works to straighten (i.e., extend) the finger but also allows the finger to bend against the force when desired, e.g., when the user desires to grasp an item. The ring is particularly well-suited to being positioned on a finger that has a boutonniere deformity.

The ring also can be constructed to be aesthetically pleasing to the user.

Other features and advantages will be apparent from the following description of the drawings and the preferred embodiments, and from the claims.

BRIEF DESCRIPTION OF THE DRAWINGS

FIG. 1 is a perspective view of a ring splint according to one embodiment.

FIG. 2 is a perspective view of the ring splint of FIG. 1 positioned on a finger that has a boutonniere deformity where the finger is in a flexed position.

FIG. 3 is a perspective view of the ring splint of FIG. 1 positioned on a finger that has a boutonniere deformity where the finger is in a relatively extended position.

FIG. 4 is a top plane view of one embodiment of a finger ring positioned on a finger of a user where the finger is in extension.

FIG. 5 is a perspective view of a ring splint according to another embodiment.

FIG. 6 is a plane view of the first side of the finger ring of FIG. 4.

FIG. 7 is a plane view of the second side of the finger ring of FIG. 4.

FIG. 8 is a perspective view of a ring splint according to another embodiment.

FIG. 9 is a perspective view of the ring splint of FIG. 8 positioned on a finger that has a boutonniere deformity where the finger is in a flexed position.

FIG. 10 is a perspective view of the ring splint of FIG. 8 positioned on a finger that has a boutonniere deformity where the finger is in a relatively extended position.

GLOSSARY

Figure 11:
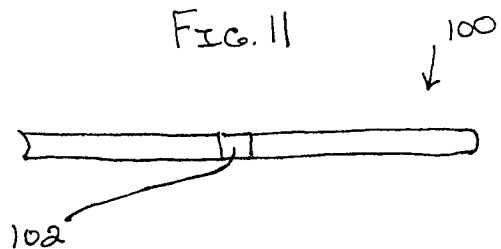
FIG. 11 is a top view of a splint according to one embodiment.

In reference to the invention, these terms have the meanings set forth below:

The term "finger" includes all digits of the hand including the thumb.

The term "boutonniere deformity" as used herein refers to a boutonniere deformity and a pseudoboutonniere deformity.

DETAILED DESCRIPTION

The ring splint includes a first loop, a second loop, a third at least partial loop, and an elongated support. The first loop is dimensioned to be capable of being positioned around the intermediate phalanx of the finger of a user. The second loop is dimensioned to be capable of being positioned around the intermediate phalanx of the finger of a user. The third loop at least partial loop is dimensioned to be capable of being positioned around a portion of the proximal phalanx of the finger of the person wearing the ring, preferably it is dimensioned to be positionable about the proximal phalanx of a finger that exhibits a boutonniere deformity. For ease of reference, the third at least partial loop will sometimes be referred to herein as the third loop. At least one of the first loop, the second loop and the third loop is connected to the elongated support to hold the support against the palmar surface of the finger when the ring splint is worn on a finger.

The elongated support is sufficiently rigid and is associated with the loops in such a way that when the splint is in position on a finger, the support exerts a force against the palmar surface of the finger. The force prevents the finger from flexing (i.e., bending) until such time as the user desires to flex the finger. The elongated support acts in combination with the loops to provide a corrective action against the finger, i.e., applies an extension force against the palmar surface of the finger. The support thus exerts a force against the palmar surface of the finger that encourages the finger to extend. In the case of a finger that exhibits a boutonniere deformity, the support exerts a force on the finger that encourages the finger to extend from its normally flexed position. The support is also sufficiently flexible (e.g., in the area of the interphalangeal joint) so as to allow the finger to flex when the user flexes his or her finger.

Referring to FIG. 1, a finger ring splint 10 that includes a first loop 12, a second loop 14, a partial loop 16, and an elongated support 20 in the form of a spring 22, is shown. A foam cushion 24 surrounds the mid-section of the spring 22 to provide a surface that is comfortable to the user. The first loop 12, the second loop 14, and the partial loop 16 are attached to the elongated support 20. The first loop 12 and the second loop 14 of the ring 10 wrap around the support 20 which helps to maintain the support 20 in a snug position against the palmar surface of a finger. The second loop 14 is part of a spiral loop that terminates in the partial loop 16. The second loop 14 spirals around the elongated support 20 and assists in maintaining the support 20 in a desired position on the finger 30. The dimensions of the loops and the support 20 assist in pulling the support 20 against the palmar surface of the finger 30. The partial loop 16 enables the ring 10 to be relatively easily positioned over the proximal interphalangeal joint (PIP) of a finger.

The second loop 14 extends at an angle to the first loop 12 and the partial loop 16 extends at an angle to the second loop 14.

A first decorative element 26 is positioned on the end of the partial loop 16 to provide an aesthetically pleasing appearance. A second decorative element 28 is positioned at the union between the first loop 12 and the second loop 14 to provide an aesthetically pleasing appearance.

Referring to FIGS. 2 and 3, the finger ring 10 is positioned on a finger 30 that has a boutonniere deformity. The first loop 12 and the second loop 14 are positioned between the proximal interphalangeal joint 32 and the distal interphalangeal joint 34 and around the intermediate phalanx 40, and the third partial loop is positioned about a portion of the proximal phalanx 38. The support 20 extends along the palmar surface 36 of the finger 30 and contacts the palmar surfaces of the proximal phalanx 38 and the intermediate phalanx 40 and exerts a force on the palmar surfaces the finger encouraging the finger 30 to achieve an extended position. In FIG. 2, the finger 30 is in a relatively more flexed position and the elongated support 20 is in a relatively non-linear position. In FIG. 3, the finger 30 is in an extended position and the elongated support 20 is in a relatively more linear position.

Other embodiments are within the claims. FIGS. 4, 6 and 7, for example, illustrate a finger ring 60 that includes a first loop 62, a second loop 64, and a third partial loop 67, in position on a finger 80 that is in an extended position. The first and second loops 62, 64 loop around the intermediate phalanx 82 of the finger. The first and second loops 62, 64 are affixed together at a union 65 that, when the ring is worn, is positioned on the dorsal surface 84 of the finger 80 between the distal interphalangeal joint 86 and the intermediate interphalangeal joint 88. A first decorative element 66 is positioned at the union 65 between the first and second loops 62, 64. The third partial loop 67 wraps around a portion of the proximate phalanx 90 and terminates in a second decorative element 68. The finger ring 60 can be worn with or without a support.

FIG. 5 illustrates an embodiment of the ring 60 that is in the form of a ring splint 61 that includes an elongated linear support 70 positioned between the first loop 62 and the second loop 64. The elongated support 70 includes a first end portion 72, a second end portion 74, and a middle portion 76. The first and second end portions 72, 74 are of a rigid material and in the form of thin elongated reeds, and the middle portion 76 is a spring. The first and second end portions 72, 74 are attached to the spring 76. A cushion (not shown) optionally surrounds the spring 76 and a portion of the first and second end portions 72, 74 to create more comfort to the user of the ring 60.

FIGS. 8-10 illustrate a ring splint 110 that includes a first loop 112, a second loop 114, a partial loop 116, and an elongated support 120 in the form of a spring 122. A foam cushion 124 surrounds the mid-section of the spring 122 to provide a surface that is comfortable to the user. The first loop 112, the second loop 114, and the partial loop 116 are attached to the elongated support 120. The first loop 112 and the second loop 114 of the ring 110 wrap around the support 120, which helps to maintain the support 120 in a snug position against the palmar surface 36 of a finger 30. The second loop 114 is part of a spiral loop that includes the second loop 114 and terminates in the partial loop 116. The second loop 114 spirals around the elongated support 120 and assists in maintaining the support 120 in a desired position on the finger 30. The dimensions of the loops and the support 120 assist in pulling the support 120 against the palmar surface of the finger 30. The partial loop 116 enables the ring 110 to be relatively easily positioned over the proximal interphalangeal joint 32 of a finger 30. The partial loop 116 includes a decorative element 126, e.g., a gem stone, attached to the terminal end thereof.

Referring to FIGS. 9 and 10, the ring splint 110 is positioned on a finger 130 that has a boutonniere deformity. The first loop 112 and the second loop 114 are positioned between the proximal interphalangeal joint 32 and the distal interphalangeal joint 34 and around the intermediate phalanx 40, and the third partial loop 116 is positioned about a portion of the proximal phalanx 38. The support 120 extends along the palmar surface 36 of the finger 30 and contacts the palmar surfaces of the proximal phalanx 38 and the intermediate phalanx 40 and exerts a force on the palmar surfaces the finger encouraging the finger 30 to achieve an extended position. In FIG. 9, the finger 30 is in a relatively more flexed position and the elongated support 120 is in a relatively non-linear position. In FIG. 10, the finger 30 is in an extended position and the elongated support 120 is in a relatively more linear position.

The loops of the ring splint can be in a variety of forms including, e.g., circular, spiral, elliptical, oval, and ovoid. The loops can be made from any material. The loop material can have a variety of properties including, e.g., being rigid, malleable, deformable, and combinations thereof. Useful loop materials include polymer (e.g., thermoset polymer, thermoplastic polymer, elastomer, and combinations thereof), composite (e.g., polymer and cellulose fiber composites, and polymer and metal (e.g., fibers, particles and fines)), metal, and combinations thereof. Suitable metals include, e.g., copper, gold, silver, aluminum, alloys, steel, iron, tin, and combinations thereof.

The elongated support can be of a variety of configurations and made from a variety of materials. The length of the support is selected to provide the support function to the finger while being comfortable to the user. Useful elongate supports include, e.g., springs, hinges, cylindrical tubes, cylindrical rods, cuboid (e.g., a rectangular paralellpiped), and combinations thereof. The ends and sides of the support can be rounded to provide comfort to the user. Useful hinged supports include, e.g., spring hinges, living hinges, hinges that include male and female components, and combinations thereof. The hinge preferably is positioned on the support and in relation to the loops such that it enables a finger to bend at its joint when the splint is in position on the finger and the user causes the finger to exert a bending force. The hinge can be positioned, for example, on the palmar surface of the interproximal joint.

Examples of useful supports include plastic splints that include an elongated member and a living hinge disposed along the elongated member and perpendicular to the longitudinal axis of the elongated member, and splints that include an elongated member having a longitudinal extent and a spring hinge disposed perpendicular to the longitudinal extent. The hinge is positioned at a location along the longitudinal extent of the support to facilitate bending.

Figure 12:
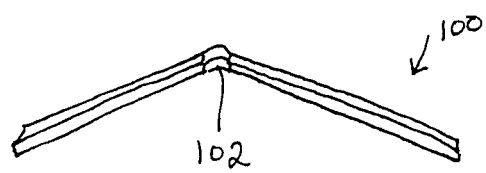
FIG. 12 is a perspective view of the splint of FIG. 11.

FIGS. 11 and 12 illustrate one embodiment of a support 100 that is in the form of a polymeric, elongated member 100 that includes a living hinge 102.

Figure 13:
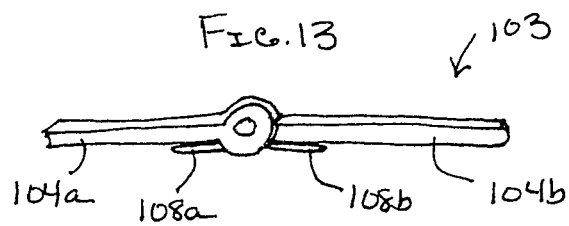
FIG. 13 is a perspective view of a splint according to another embodiment.
Figure 14:
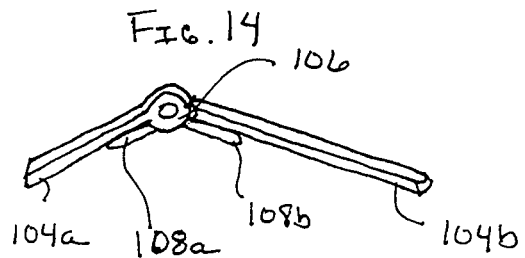
FIG. 14 is a perspective view of the splint of FIG. 13 in a bent position.

In another embodiment, the support 103 includes two elongated members 104a, 104b joined together through a spring hinge 106, as illustrated in FIGS. 13 and 14. The ends 108a, 108b of the spring hinge 106 exert a force against the elongated members 104a, 104b, which pushes the elongated members 104a, 104b away from each other toward a more open, i.e., linear, position, as illustrated in FIG. 13. When in position on a finger, the flexing of the finger forces the elongated members 104a, 104b toward each other while the force of the spring exerts a countering force which creates resistance to the movement but does not prevent the flexing movement, as illustrated in FIG. 14.

The support can be made from a variety of materials including, e.g., metal (e.g., alloys, stainless steel, spring steel, copper, gold, silver, tin, aluminum, and combinations thereof), polymer (e.g., thermoplastic polymers, thermoset polymers, thermoplastic elastomers, polyethylene, polypropylene, polyester, polystyrene, polyamide, elastomers (e.g., styrene-butadiene-rubber, styrene-isoprene-styrene, styrene-butadiene-styrene, styrene-ethylene-butene-styrene, styrene-ethylene-propene-styrene, silicone rubber and combinations thereof), composites (e.g., cellulose and polymer composites, and metal and polymer composites), wood, foam, and combinations thereof.

The support can be attached to the loops in a variety of configurations including, e.g., removably attached (i.e., the splint can be removed from the ring splint without damaging the ring) and permanently attached (i.e., removing the support would damage the ring). In one embodiment, the support is removably attached to at least one loop such that the support can easily slide into and out of position between the loops and the palmar surface of the finger. Removably attached supports can be configured to enable the support to be removed from the ring splint and replaced on the ring splint. Removable supports allow a user to replace the support with a relatively more rigid or less rigid support, and to replace the support when the support becomes soiled or worn.

The components (e.g., the loops, the support, the decorative components, and the cushion), of the ring can be attached to each other using any suitable mechanism including, e.g., mechanical devices, e.g., wires, fibers, staples, and clips, adhesive compositions (e.g., adhesive backed-tapes), welds (e.g., metal and polymer), snap fit mechanisms, friction fit mechanism, male-female connectors, and combinations thereof.

A protective element is optionally positioned on the support to protect the user from any pain or discomfort that might be caused by the support or movement of the support while it is in position on the finger. When the support includes a spring element, for example, the protective element can protect the user's skin from being pinched by the springs. The protective element can surround all or a portion of the support and can be positioned to provide comfort to the user. Useful protective elements include, e.g., the optional cushion described above, sleeves (e.g., a sleeve that at least partially or even completely surrounds a portion of the support (e.g., the skin contacting portion of the support), or even the entire support), and combinations thereof. Useful materials from which the protective element can be formed include, e.g., plastic (e.g., polymer films and coatings), elastomers (e.g., styrene-butadiene-rubber, styrene-isoprene-styrene, styrene-butadiene-styrene, styrene-ethylene-butene-styrene, styrene-ethylene-propene-styrene, rubber, ethylene propylene diene rubber, silicone rubber, and combinations thereof), foam (e.g., closed cell foam and open cell foam), cotton, gauze, adhesive tape (e.g., fibrous tape, medical tape, masking tape, painter's tape, and duct tape), and combinations thereof.

Although the third at least partial loop has been described and illustrated as a partial loop, in some embodiments it is in the form of a complete loop.

Although the ring splint has been described in reference to being positioned on a single finger, the splint and its components can be configured (e.g., dimensioned) to be positioned around more than one finger.

The elongate support can extend from the proximal phalanx to the intermediate phalanx, and optionally to the distal phalanx, from the intermediate phalanx to the distal phalanx, and combinations thereof. The ring can optionally include more than one elongate support and the elongate supports can be of the same or different constructions, materials, and dimensions relative to each other.

The decorative element can be of a variety of materials, shapes and sizes including, e.g., gem stone, metal, glass, flowers, geometric shapes, and combinations thereof.

All references referred to herein are incorporated herein.

What is claimed is:

1. A ring splint comprising:
   a first metal loop;
   a second metal loop;
   a third at least partial loop; and
   an elongated support,
   the first loop and the second loop being attached to the elongated support,
   the elongated support exhibiting a rigid property and a flexible property such that the elongated support
      is configured to maintain a finger in at least partial extension when the ring splint is on a finger and the elongated support is in contact with a palmar surface of the finger, and
      to flex when the user bends the finger.

2. The ring splint of claim 1, wherein the second loop terminates in the third at least partial loop.

3. The ring splint of claim 1, wherein the first loop is attached to the second loop.

4. The ring splint of claim 1, wherein the elongated support comprises a hinge.

5. The ring splint of claim 1, wherein the elongated support comprises at least one of a living hinge and a spring hinge.

6. The ring splint of claim 1, wherein the elongated support comprises a spring.

7. The ring splint of claim 1, wherein the elongated support comprises a spring comprising a first end and a second end, a first elongate section attached to the first end of the spring, and a second elongate section attached to the second end of the spring.

8. The ring splint of claim 1, wherein the elongated support comprises a longitudinal extent and a cushion enveloping at least a portion of the longitudinal extent.

9. The ring splint of claim 1, wherein the elongated support is removably attached to the first and second loops.

10. The ring splint of claim 1, wherein the elongated support is repeatedly repositionable within the first and second loops.

11. The ring splint of claim 1, wherein when the ring splint is in position on the finger the support is positioned between the palmar surface of the finger and the first and second loops.

12. The ring splint of claim 1 further comprising an ornamental component.

13. The ring splint of claim 1 further comprising an ornamental component on at least one of the second loop and the third at least partial loop.

14. A method of using the ring splint of claim 1, the method comprising:

positioning the third at least partial loop around a portion of the proximal phalanx of a finger,
positioning the second loop around the intermediate phalanx,
positioning the first loop around the intermediate phalanx, and
positioning the elongated support against at least a portion of the palmar surface of the finger.

15. A finger ring comprising:
   a first loop;
   a second loop; and
   a third at least partial loop;
   the first loop and the second loop being attached to one another at a first location, the third loop extending from the second loop,
   the finger ring being configured such that when the finger ring is positioned on a finger, the first loop loops around the intermediate phalanx of the finger, the second loop loops around the intermediate phalanx of the finger, the third at least partial loop loops around a portion of the proximal phalanx of the finger and the first location is positioned on the dorsal surface of the intermediate phalanx of the finger.

16. The finger ring of claim 15, wherein the third at least partial loop forms a spiral with the second loop.

17. The finger ring of claim 15, wherein the third at least partial loop is attached to the second loop.

18. A ring splint comprising:
   a first metal loop;
   a second metal loop extending at an angle relative to the first loop;
   a third at least partial loop extending at an angle relative to the second loop; and
   an elongated support attached to the first loop and the second loop, the elongated support being attached to the first loop and the second loop at at least one area of attachment and having a longitudinal extent extending beyond all areas of attachment between all loops and the elongated support.

19. The ring splint of claim 18, wherein the elongated support is configured to contact a palmar surface of a finger when the ring splint is worn on the finger.

20. A ring splint comprising:
   a first metal loop;
   a second metal loop, the first loop being attached to the second loop;
   a third at least partial loop; and
   an elongated support attached to the first and second loops and exhibiting rigid properties and flexible properties such that the elongated support
      is configured to maintain a finger in at least partial extension when the splint is in position on a finger and
      to flex when the user bends the finger.

* * * * *